(12) United States Patent
Leshchiner et al.

(10) Patent No.: US 8,247,390 B2
(45) Date of Patent: Aug. 21, 2012

(54) MODIFIED HYDROPHILIC POLYMERS CONTAINING HYDROPHOBIC GROUPS

(75) Inventors: Adelya K. Leshchiner, Cresskill, NJ (US); Nancy E. Larsen, Highland Mills, NY (US); Edward G. Parent, North Bergen, NJ (US)

(73) Assignee: LuroMed LLC, Orangeburg, NY (US)

( * ) Notice: Subject to any disclaimer, the term of this patent is extended or adjusted under 35 U.S.C. 154(b) by 331 days.

(21) Appl. No.: 12/586,716

(22) Filed: Sep. 28, 2009

(65) Prior Publication Data

US 2011/0076243 A1    Mar. 31, 2011

(51) Int. Cl.
*A01N 43/04* (2006.01)
*A61K 31/715* (2006.01)

(52) U.S. Cl. .......................................... 514/54; 424/59

(58) Field of Classification Search .................. None
See application file for complete search history.

(56) References Cited

U.S. PATENT DOCUMENTS

| | | | |
|---|---|---|---|
| 4,582,865 A | 4/1986 | Balazs et al. | |
| 4,605,691 A | 8/1986 | Balazs et al. | |
| 4,636,524 A | 1/1987 | Balazs et al. | |
| 5,143,724 A | 9/1992 | Leshchiner et al. | |
| 5,246,698 A | 9/1993 | Leshchiner et al. | |
| 5,399,351 A | 3/1995 | Leshchiner et al. | |
| 5,633,001 A | 5/1997 | Ågerup | |
| 5,911,980 A | 6/1999 | Samour et al. | |
| 6,218,373 B1 | 4/2001 | Falk et al. | |
| 6,235,312 B1 | 5/2001 | Hobbs et al. | |
| 6,316,011 B1 | 11/2001 | Ron et al. | |
| 6,495,149 B1 | 12/2002 | Scavone et al. | |
| 6,509,322 B2 | 1/2003 | Benedetti et al. | |
| 6,719,740 B2 | 4/2004 | Burnett et al. | |
| 6,746,689 B2 | 6/2004 | Fischer et al. | |
| 6,824,785 B1 | 11/2004 | Kitson et al. | |
| 7,521,434 B2 | 4/2009 | Leshchiner et al. | |
| 7,858,000 B2 * | 12/2010 | Winterton | 264/1.38 |
| 2003/0099712 A1 * | 5/2003 | Jayaraman | 424/486 |
| 2004/0091604 A1 * | 5/2004 | Dempsey et al. | 427/2.27 |
| 2006/0280809 A1 | 12/2006 | Leshchiner et al. | |
| 2006/0293277 A1 * | 12/2006 | Leshchiner et al. | 514/54 |
| 2007/0036745 A1 | 2/2007 | Leshchiner et al. | |
| 2010/0276638 A1 * | 11/2010 | Liu et al. | 252/301.35 |

FOREIGN PATENT DOCUMENTS

EP    0224987 A2    6/1987

OTHER PUBLICATIONS

Tomihata et al. "Preparation of cross-linked hyaluronic acid films of low water content" Biomaterials, 1997, vol. 18, pp. 189-195.*
Mensitieri et al. (Journal of Material Science: Materials in Medicine (1994), 5(9&10), 743-7).
Schwarz et al. (Proceedings of the National Academy of Sciences of the United States of America, (May 1973) vol. 70, No. 5, pp. 1608-1612 (Abstract Sent).
Takigami, et al.; Carbohydrate Polymers 26 N:11-18 (1995).

* cited by examiner

*Primary Examiner* — Johann Richter
*Assistant Examiner* — Daniel L Branson
(74) *Attorney, Agent, or Firm* — Nutter McClennen & Fish LLP; Konstanin Linnik

(57) ABSTRACT

Disclosed are hydrophilic polymers such as polysaccharides, including hyaluronic acid of any origin, modified by reaction with epoxy-functional-silicones. Hydrophobic silicon, which contains chemically active groups covalently attach to the backbone of the hydrophilic polymer and gives these new, modified polymers the ability to dissolve hydrophobic compounds including oils, drugs, and vitamins, while maintaining the hydrophilic properties and benefits of the unmodified polymer. With respect to topical applications these polymers substantially increase the stability of formulations and provide for ease of preparation. The properties and advantages of the original polymer are maintained while other properties are augmented, namely the ability to combine with or dissolve hydrophobic and hydrophilic drugs. The products can be used alone or in combination with other substances for various applications including cosmetic, medical, and drug delivery applications. Also disclosed are methods for preparing them.

12 Claims, No Drawings

MODIFIED HYDROPHILIC POLYMERS CONTAINING HYDROPHOBIC GROUPS

CROSS-REFERENCE TO RELATED APPLICATIONS

Not Applicable

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

REFERENCE TO A MICROFICHE APPENDIX

Not Applicable

BACKGROUND OF THE INVENTION

1. Field of the Invention

The present invention relates to modified hydrophilic polymers such as hyaluronic acid, also known as hyaluronan and mixtures thereof, containing hydrophobic silicone groups prepared by reaction of the hydrophilic polymer with epoxy-functional-silicones, their preparation and compositions containing them.

2. Description of Related Art

Relevant prior art includes the following references: U.S. Pat. No. 7,521,434 discloses cross-linked gels of hyaluronic acid with hydrophobic polymers and processes; Mensitieri et al. Journal of Material Science; Materials in Medicine (1994) pages 743-747; The rheological behavior of animal vitreus and its comparison with vitreal substitutes; and Schwarz, K. Proc Nat Acad Sci (1973) Vol 70 pp 1608-1612; A Bound form of Silicon in Glycosaminoglycans and Polyuronides.

Hyaluronic acid (HA) and its derivatives are important materials used in the medical and cosmetic industry. Their unique viscoelastic properties combined with their high water binding properties and exceptional biocompatibility have led to a wide variety of products in the ophthalmic, arthritis, wound healing, anti-adhesion, drug delivery, soft tissue augmentation, and burn management fields, as well as use in topical cosmetic moisturization. It is an excellent biomaterial for a variety of combined uses the medical field due to its viscoelastic and biocompatibility properties. The water binding and hydration properties of hyaluronic acid provide water to the skin. This moisturizing effect is widely used in the cosmetic industry.

Hyaluronic acid is a naturally occurring polysaccharide that consists of alternating N-acetyl-D-glucosamine and D-glucuronic acid monosaccharide units linked with alternating [beta] 1-3 glucoronidic and [beta] 1-4 glucosaminidic bonds. The molecular weight of hyaluronic acid is generally within the range of 50,000 up to more than 8,000,000

Hyaluronic acid is found in all vertebrates—in the skin, vitreous humor, the synovium, the cartilage, and the umbilical cord. It is not species specific and therefore highly biocompatible. It is known for its efficiency of hydration, it has a binding capacity of up to 20 times its weight in water and it is the natural moisturizer in the cell matrix of the skin. It typically exists at concentrations of 200 micrograms per gram of dermal tissue. Cross-linking of HA has been used to improve the physical properties of the molecule and to enhance its properties for various uses, or to immobilize the HA to various supports for medical purposes including the diagnosis of male infertility. Formulations of hyaluronic acid have been used by the cosmetic industry as skin moisturizers. One important use of hyaluronic acid and its derivatives is founded in its properties as a drug delivery vehicle. Various drug and other biological actives have been loaded into hydrogels of HA and its derivatives; however there are some limitations on the types of substances capable of being loaded based on their chemical nature. Hydrogels composed largely of water have difficulty accepting substances of hydrophobic nature. Some organic solvents used to solubilize a hydrophobic substance will dehydrate the hydrogel or precipitate the HA. Some methods have been developed to overcome this problem although there is still difficulty with some substances. Hyaluronic acid has been used for delivery of drugs such as diclofenac.

Silicones are also a very versatile class of compounds used for many applications in the medical field and cosmetic industry. Topical application of silicones have been used for wound healing, drug delivery and burn treatment and are also topically used in cosmetic formulations. Silicones are in general, hydrophobic and their moisturizing properties are due to their ability to provide a vapor barrier to the skin.

Silicone Gels are also used for delivery purposes in the medical field and the cosmetic industry. Their hydrophobic nature makes them excellent vehicles for incorporating hydrophobic substances. Silicone implants are used to deliver contraceptives and other hydrophobic drugs.

BRIEF SUMMARY OF THE INVENTION

The invention provides, in one aspect thereof, chemically modified products of hydrophilic polymers and one or more silicone containing compounds. The hydrophilic polymer may be a natural or synthetic polysaccharide, including heparin, heparin sulfate, chondroitin, chondroitin sulfate, hyaluronic acid, hydroxyethyl cellulose, carboxymethyl cellulose and an alginates. The compositions of the invention may also contain one or more hydrophobic substances, including oils, silicones, sun screens, antibiotics and steroids.

In another aspect, the invention provides methods for making the modified products by subjecting them to reaction with an epoxy functionalized silicone compound in an aqueous alkaline solution at a temperature of about 20° C. The HA concentration before reaction with the epoxy compound may range from 20% to 0.01%, preferably about 3%. The molar ratio of the epoxy silicone compound to HA may range from 1:20 to 4:1, and preferably about 2:1. It should be noted that excess epoxy silicone can be used to drive the reaction forward. By this is meant that even though at a given range of a 4:1, the molar ratio is actually in excess of the needs at reactive sites, one can continue to add more reactive epoxy which will affect of kinetics, i.e., driving the reaction forward, even though the amount of reactant that will react is limited.

The compositions of the present invention combine the advantages of both hyaluronic acid and silicone gels in that they contain both hydrophobic and hydrophilic moieties. The modified hyaluronic acid has the ability to incorporate both large volumes of water and hydrophilic substances as well as hydrophobic substances such as oils, sun screens, vitamins, antibiotics, steroids and other drugs. Thus, there is provided an improved drug delivery vehicle. The nature of the material also provides a composition which is hydrophobic in nature and is thus easier to formulate in a cosmetic composition.

DETAILED DESCRIPTION OF THE INVENTION

The present invention provides for the preparation of compositions of chemically modified polysaccharides prepared in the presence of an epoxy functionalized silicone compound, wherein the ratio of the silicone compound to the polysaccharide is 1:20 to 4:1, and the concentration of the polysaccharide in the aqueous solution is from 0.05 to 100 mg/ml.

The present invention relates to compositions prepared by the process of incorporating the silicone compound through an epoxy functionalized silicone compound and conducting a chemical reaction in the presence of the polysaccharide such as hyaluronan (HA).

The present invention provides compositions of polysaccharide products prepared with an epoxy functionalized silicone compound in the family of epoxy functionalized silicones such as 2(3,4 epoxycyclohexyl)ethyltrimethoxysilane, epoxypropoxypropyl terminated polydimethylsiloxane, tris (glycidoxypropyldimethylsiloxy) phenylsilane, mono-(2,3-epoxy) propylether terminated polydimethylsiloxane-120 cSt, epoxycyclohexylethyl terminated polydimethylsiloxane, 25-35 cSt and glycidoxypropyltrimethoxysilane.

The products of the invention are prepared by reacting the epoxy silicone compound or compounds in the presence of the polysaccharide such as hyaluronan (HA) to obtain a modified polysaccharide. More than one epoxy functionalized silicone can be used, each having a variety of properties that contribute to the final product; for example by changing the hydrophobic-hydrophilic nature, contributing to the charge of the molecule, or the final viscosity of the product.

The silicon compound incorporated may also be a group capable of undergoing further polymerization or reactions with new functional groups such as trialkoxysilanes, dialkoxysilanes, monoalkoxysilanes, and vinyl groups, added, allowing further modification of the product.

The present invention provides for a material that can be used alone or with other substances which may be added to enhance the properties for a particular purpose. These products may be added or covalently bound substances that can be applied for numerous applications including, for the use in cosmetic, medical, and drug delivery fields.

The present invention provides for a biocompatible material, such materials which may be useful as a stable form of implants. HA implants have limited duration since natural mechanisms for the clearance from the body; a more resistant implant can improve the efficacy and durability of devices used for soft tissue augmentation, drug delivery, anti-adhesion, ophthalmic, and anti-arthritis.

The present invention provides for a topical composition with a hydrating effect on the skin. Hyaluronic acid provides a high water binding capacity, typically 20 grams of water per gram of hyaluronic acid, such a composition will provide a high degree of moisturization to the skin. Compositions of hyaluronic acid have been used to promote wound healing and reduce scaring. Silicone gels and semi-occlusive membranes are commercially available, e.g., Cica Care Silicone Gel Dressing Sheeting—by Cica Care, ScarAway Professional Grade Silicone Scar Treatment Sheets by Mitchell-Vance Laboratories and ScarErase by ScarErase. Inc. for the treatment of chalets and hypertrophic scars. It is believed that silicon membranes create a barrier impermeable to water thereby creating a moisturization effect reducing scarring.

The present invention is based on hyaluronic acid, a naturally occurring polysaccharide in the human body. It is a common constituent in the tissues and is highly biocompatible. Since the molecule is not species specific it is not antigenic and therefore non-immunogenic. The normal content of hyaluronic acid in the skin is 0.2 mg/gram of tissue, although since it is limited to the extracellular space the concentration of HA in the fluid of the extracellular space is actually about 2.5 mg/ml in concentration. It can therefore be appreciated that the present invention will be a non-inflammatory non-irritating biologically acceptable treatment.

The following examples will further illustrate the invention in more detail.

EXAMPLES

Example 1

4.00 gms of sodium hyaluronate (HA from viable hemolytical streptococci, Molecular Weight 1.93 million.) were mixed for one day with 96 gms of deionized water to give a 4.0% solution of HA. 7.5 ml of 2.0 M NaOH were then added to the mixture and stirred on a Silverson High Shear Mixer, for 1 minute using a low-shear-head at 400 rpm. Then, 2.5 gms of 2(3,4 epoxycyclohexyl)ethyltrimethoxysilane were added. The sample was mixed for 1 minute using a low-shear-head at 400 rpm on a Silverson High Shear Mixer. The pH was adjusted to 12 by the addition of 2.0% HCl while mixing. The reaction was allowed to continue for four hours before neutralizing the reaction mixture by the addition of 70 ml 2.0% HCl. The final volume was 182.00 gms. The product was washed in dialysis tubing against 2 kg of distilled water, and the water was exchanged 5 times. 182.00 gms of a creamy white product were formed.

Example 2

15 gms of sodium hyaluronate (HA from viable hemolytical streptococci, Molecular Weight 1.93 million.) were suspended in 150 ml of methanol. 225 ml of distilled water and 30 ml of 0.2 M NaOH were added to hydrate the HA. Then, 7.5 gms of 2(3,4 epoxycyclohexyl)ethyltrimethoxysilane were added and stirred for 15 minutes. 150 ml of 50% methanol in water were added and stirring continued. After 30 min the pH was reduced to 9 by the addition of 14 ml of 2% HCL. The reaction was continued for 2 hours. The reaction product was neutralized to pH 7 with 2% HCL, and the volume adjusted to 1500 ml by the addition of distilled water. The product was placed into dialysis vs 20 kg of distilled water. The wash water was exchanged 3 times over 2 days. 1626 gms of a creamy white product were formed.

Example 3

This example illustrates the preparation of a modified HA/silicone product prepared under aqueous conditions. 15.00 gms of sodium hyaluronate (Microbial Fermented HA, Molecular Weight 2.07 million.) were mixed for one day with 485 gms of deionized water and the HA was allowed to hydrate overnight to give a 3.0% solution of HA. 42.5 ml of 2.0 M NaOH were then added to the mixture and stirred with a kitchen aid mixer, for 10 minutes stirred at low speed until a smooth consistency was obtained. Then, 12.5 gms of mono-(2,3-epoxy) propylether terminated polydimethylsiloxane-120 cSt were added. The sample was mixed for 45 minutes using a kitchen aid mixer at low speed. The pH was adjusted to 12 by the addition of 2.0% HCl while mixing. The reaction was allowed to continue for two hours before neutralizing by the addition of 355 ml 2.0% HCl. The mixture was brought up to 1 kg with water and was washed in dialysis tubing against 20 L of distilled water. The wash water was exchanged 5 times over 2 days. 1565 gms of a creamy white product having a smooth and silky feel were formed.

Example 4

This example illustrates the preparation of a modified HA/silicone product prepared under aqueous conditions. 15.00 gms of sodium hyaluronate (Microbial Fermented HA, Molecular Weight 2.07 million.) were mixed for one day with 485 gm of deionized waters and allowed the HA to hydrate overnight to give a 3.0% solution of HA. 42.5 ml of 2.0 M NaOH were then added to the mixture and stirred with a kitchen aid mixer for 10 minutes stirred at low speed until a smooth consistency was obtained. Then, 12.5 gms of epoxycyclohexylethyl terminated polydimethylsiloxane, 25-35 cSt were added. The sample was mixed for 45 minute using a kitchen aid mixer at low speed. The pH was adjusted to 12 by the addition of 2.0% HCl while mixing. The reaction was allowed to continue for two hours before neutralizing by the addition of 355 ml 2.0% HCl. The mixture was brought up to 1 kg with water and was washed in dialysis tubing against 20 L of distilled water. The wash water was exchanged 5 times over 2 days. 1187 gms of a creamy white product having a smooth and silky feel was formed.

Example 5

This example illustrates the preparation of a modified HA/silicone product prepared under aqueous conditions. 3.00 gms of sodium hyaluronate (Microbial Fermented HA, Molecular Weight 2.07 million.) were mixed for one day with 97 gms of deionized water and the HA was allowed to hydrate overnight to give a 3.0% solution of HA. 14.5 ml of 0.2 M NaOH were then added to the mixture and stirred at 800 rpm with a Lightnin brand overhead mixer for 10 minutes, stirred at low speed until a smooth consistency was obtained. Then, 0.2 gram of glycidoxypropyltrimethoxysilane (Dow Corning Z-6040) was added. The sample was mixed for 45 minute at 800 rpm with a Lightnin overhead mixer. The pH was adjusted to 12 by the addition of 2.0% HCl while mixing. The reaction was allowed to continue for two hours before being neutralized by the addition of 8 ml 2.0% HCl. The mixture was brought up to 200 ml with water and 150 ml were washed in dialysis tubing against 10 L of distilled water. The wash water was exchanged 5 times over 2 days. 247 gms of a clear transparent product were formed.

Example 6

This example illustrates the preparation of a modified HA/silicone product prepared under aqueous conditions. 15.00 gms of sodium hyaluronate (Microbial Fermented HA, Molecular Weight 2.07 million.) were mixed for one day with 485 gms of deionized water and the HA was allowed to hydrate overnight to give a 3.0% solution of HA. 42.5 ml of 2.0 M NaOH were then added to the mixture and stirred with a kitchen aid mixer, for 10 minute stirred at low speed until a smooth consistency was obtained. Then, 12.5 gms of 2(3,4 epoxycyclohexyl)ethyltrimethoxysilane were added. The sample was mixed for 45 minute with a kitchen aid mixer at low speed. The pH was adjusted to 12 by the addition of 2.0% HCl while mixing. The reaction was allowed to continue for two hours before being neutralized by the addition of 355 ml 2.0% HCl. The mixture was brought up to 1 kg with water and was washed in dialysis tubing against 20 L of distilled water. The wash water was exchanged 5 times over 2 days. 1248 gms of a creamy white product having a smooth and silky feel were formed. The product was preserved with 6.25 gram of phenonip.

Example 7

Five glass vials filled with 20 ml of the sample prepared in Example 2, and placed in an incubator at 37° C. or stored in the dark at room temperature (22° C.). A vial was removed at each of 1, 5, 8, and 12 month time points to monitor changes in appearance, consistency, pH, and viscosity of the product. The viscosity was measured on a Brookfield DV II+ Pro viscometer, Spindle #25 with a small cup adapter and a shear rate of 13.2 sec-1, at 25° C.

No significant changes in the sample were noted over one year. Only a small decrease was noted in the viscosity, indicating that the product was stable.

| 37° C. Stability Study | | | | | |
|---|---|---|---|---|---|
| Time point (months) | Appearance | Consistency | pH | Viscosity | % change |
| 0 | No change | No change | 7.5 | 2362 | 0 |
| 1 | No change | No change | 7.5 | 2404 | +1.8 |
| 5 | No change | No change | 7.5 | 2475 | +4.8 |
| 8 | No change | No change | 7.5 | 2302 | −2.5 |
| 12 | No change | No change | 7.5 | 2194 | −7.1 |

| 22° C. Stability Study | | | | | |
|---|---|---|---|---|---|
| Time point (months) | Appearance | Consistency | pH | Viscosity | % change |
| 0 | No change | No change | 7.5 | 2362 | 0 |
| 1 | No change | No change | 7.5 | 2491 | +5.5 |
| 5 | No change | No change | 7.5 | 2487 | +5.3 |
| 8 | No change | No change | 7.5 | 2364 | −0.2 |
| 12 | No change | No change | 7.5 | 2358 | −7.1 |

Example 8

The product Example 6 was sent for a Human Repeat Insult Patch Test to an independent lab in order to determine if the material causes any irritation or allergic reaction. The skin of 50 subjects were tested, 24 hour exposures to the product made in Example 6 three times a week for three consecutive weeks. The skin was evaluated after each application. Following a 10-14 day rest, a retest/challenge dose was applied an evaluated after 48 and 96 hours. The test sites were scored according to standards set by The International Contact Dermatitis Research Group (ICDRG). No adverse reactions of any kind were reported. There were no signs or symptoms of sensitization (contact dermatitis).

Example 9

This example illustrates the preparation of a formulation with a product prepared in Example 2 plus hydrophobic compounds and 49.5% water.

| Part | Ingredient | Percent by Weight | Grams required |
|---|---|---|---|
| A | product in Example 2 | 44.0 | 44.0 |
|   | Parsol MCX | 2.5 | 2.5 |
|   | Silicone Fluid 200 | 2.5 | 2.5 |
|   | phenonip | 0.5 | 0.5 |
|   | water | 49.5 | 49.5 |
| B | Carbopol 934 | 0.5 | 0.5 |
| C | Triethanolamine | 0.5 | 0.5 |

44 gms of the product prepared in example 2 were added to the remaining ingredients in part A. The mixture was stirred until completely mixed. Part A and Part B were mixed and placed on a shaker overnight. Triethanolamine was then added to create a thick cosmetic cream.

Example 10

This example illustrates the preparation of a formulation with a product prepared in Example 3 plus hydrophobic compounds and 49.5% water.

| Part | Ingredient | Percent by Weight | Grams required |
|---|---|---|---|
| A | product in Example 3 | 44.0 | 44.0 |
|   | Parsol MCX | 2.5 | 2.5 |
|   | Silicone Fluid 200 | 2.5 | 2.5 |
|   | phenonip | 0.5 | 0.5 |
|   | water | 49.5 | 49.5 |
| B | Carbopol 934 | 0.5 | 0.5 |
| C | Triethanolamine | 0.5 | 0.5 |

44 gms of the product prepared in example 3 were added to the remaining ingredients in part A. The mixture was stirred until completely mixed. Part A and Part B were mixed and placed on a shaker overnight. Triethanolamine was then added to create a thick cosmetic cream.

Example 11

This example illustrates the preparation of a formulation with a product prepared in Example 2.

| Part | Ingredient | Percent by Weight | Grams required |
|---|---|---|---|
| A | product in Example 2 | 79.2 | 79.2 |
|   | Carbopol 934 | 0.5 | 0.5 |
| B | Vitamin E | 3.96 | 3.96 |
|   | Parsol MCX | 3.96 | 3.96 |
|   | Silicon Quat Microemultion | 11.08 | 11.08 |
| C | Triethanolamine | 0.5 | 0.5 |
| D | Roseoil W/S | 0.3 | 0.3 |
|   | Phenonip | 0.5 | 0.5 |

79.2 gms of the product prepared in example 2 were mixed with Carbopol 934 in part A The mixture was stirred until completely mixed. Part B was prepared by mixing the ingredients in Part B using a lab mixer. Part A and Part B were combined and mixed until uniform. Triethanolamine in Part C was then added to create a thick cosmetic cream. Roseoil W/S and Phenonip in Part D were added.

Example 12

This example illustrates the preparation of a formulation with a product prepared in Example 2 and 44.5% Petrolatum.

| Part | Ingredient | Percent by Weight | Grams required |
|---|---|---|---|
| 1 | product in Example 2 | 20 | 20 |
|   | water | 20 | 20 |
| 2 | Carbopol 934 | 0.3 | 0.3 |
| 3 | Petrolatum | 44.5 | 44.5 |
|   | Vitamin E acetate | 5.0 | 5.0 |
|   | Parsol MCX | 7.4 | 7.4 |
| 4 | Triethanolamine | 0.3 | 0.3 |
|   | 1% Sodium Hyaluronate in Water | 2 | 2 |
| 5 | phenonip | 0.5 | 0.5 |

In part 1, 20 gms of the product prepared in example 2 were added to 20 gms of water and mixed until a uniform viscous solution formed. 0.3 gm of Carbopol 934 was added to the mixture in part 1 and mixed using a lab stirrer for 20 minutes until a uniform dispersion formed. 45 gms of petrolatum were mixed with 5 gms of Vitamin E acetate and 7.4 gms of Parsol MCX in part 3 and heated to 60° C. while mixing and continued until a clear mixture was obtained. The mixture obtained in Part 2 was heated to 60° C. The mixtures obtained in Part 2 and Part 3 were combined and cooled to 30° C. 1% Sodium Hyaluronate in water and triethanolamine in part 4 were mixed with the 30° C. mixture and stirred until thickened. Phenonip (0.5 gram) was added as a preservative.

Example 13

This example illustrates the preparation of a formulation with a product prepared in Example 2.

| Part | Ingredient | Percent by Weight | Grams required |
|---|---|---|---|
| A | Vitamin E | 5.0 | 5.0 |
|   | Robane | 4.0 | 4.0 |
|   | Silicon Quat Microemultion | 8.0 | 8.0 |
|   | Parsol MCX | 5.0 | 5.0 |
|   | Triethanolamine | 0.4 | 0.4 |
| B | product in Example 2 | 64.4 | 64.4 |
|   | Carbopol 934 | 0.4 | 0.4 |
| C | Water | 10.0 | 10.0 |
|   | Glycerol | 2.0 | 2.0 |
| D | phenonip | 0.5 | 0.5 |
|   | Rose Natural water soluble | 0.3 | 0.3 |

In part A 5 gms of Vitamin E, 4 gms of Robane, 8 gms of Quat silicone microemulsion, and 5 gms of Parsol MCX were combined and mixed until a uniform mixture was obtained. 0.4 gm of Triethanolamine was added and mixed thoroughly. The ingredients in Part B were mixed in a separate container, 0.4 gm of Carbopol 934 was dispersed into 64.4 gram of the product obtained in Example 2 and stirred until completely mixed. Water and Glycerol in Part C were mixed together then combined with Part B and thoroughly mixed. The mixture comprising Part B and Part C was Mixed with Part A and stirred until a thick uniform mixture was obtained. Phenonip (0.5 gram) was added as a preservative. Rose natural water soluble was added at the end.

The invention claimed is:

1. A composition comprising a polysaccharide, said polysaccharide being a modified hyaluronic acid, a silicone compound, wherein the composition is prepared by a process of incorporating the silicone compound through an epoxy functionalized silicone compound while conducting a chemical reaction in the presence of hyaluronate.

2. The composition of claim 1, wherein the chemical reaction is conducted with the molar ratio of the epoxy silicone compound to the polysaccharide is 1:20 to 4:1 and the concentration of the polysaccharide in the aqueous solution is from 0.05 to 100 mg/ml.

3. The composition of claim 1, wherein the epoxy functionalized compound is selected from 2(3,4 epoxycyclohexyl)ethyltrimethoxysilane, epoxypropoxypropyl terminated polydimethylsiloxane and tris-(glycidoxypropyldimethylsiloxy)-phenylsilane.

4. The composition of claim 1, wherein the hyaluronate is sodium hyaluronate.

5. A method of treating a mammal with dermatitis comprising topically applying a therapeutically effective amount of the composition according to claim 1 containing hydrocortisone at a concentration of about 1% to the affected area.

6. A method of treating the skin of a mammal to prevent sunburn comprising topically applying a therapeutically effective amount of the composition according to claim 1 containing the sun screen Parsol MCX at a concentration of about 7.5% to the affected area.

7. A method of treating a mammal with dermal abrasion comprising topically applying a therapeutically effective amount of the composition according to claim 1 containing bacitracin at a concentration of about 500 units per gram to the affected area.

8. A method of preparing the composition of claim 7, said method comprising subjecting sodium hyaluronate in a dilute aqueous alkaline solution at a pH of not less than about 9 to a reaction with an epoxy functionalized silicone compound at about 20° C.

9. A method of preparing the composition of claim 7, said method comprising subjecting a mixture of sodium hyaluronate in a dilute aqueous alkaline solution containing a suitable solvent solution at a pH of not less than about 9 to a reaction with an epoxy functionalized silicone compound at about 20° C.

10. The method according to claim 9, wherein the suitable solvent is selected from the group consisting of alcohols, ketones, dimethyl sulfoxide, dimethylformamide, tetrahydrofuran.

11. The method according to claim 10, wherein the suitable solvent is methanol.

12. The method according to claim 8, wherein the molar ratio of the epoxy silicone compound to sodium hyaluronate is from 1:20 to 4:1, and the concentration of the sodium hyaluronate in the aqueous solution is from 0.05 to 100 mg/ml.

* * * * *